United States Patent
Oster

(10) Patent No.: US 9,433,756 B2
(45) Date of Patent: Sep. 6, 2016

(54) ANCHOR SLEEVE DEPLOYMENT FOR IMPLANTABLE MEDICAL DEVICES

(71) Applicant: Medtronic, Inc., Minneapolis, MN (US)

(72) Inventor: Daniel C. Oster, Blaine, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 191 days.

(21) Appl. No.: 14/450,923

(22) Filed: Aug. 4, 2014

(65) Prior Publication Data

US 2015/0045807 A1 Feb. 12, 2015

Related U.S. Application Data

(60) Provisional application No. 61/864,138, filed on Aug. 9, 2013.

(51) Int. Cl.
*A61M 5/32* (2006.01)
*A61M 25/04* (2006.01)
*A61B 17/34* (2006.01)
*A61M 25/00* (2006.01)
*A61N 1/05* (2006.01)
*A61M 25/02* (2006.01)

(52) U.S. Cl.
CPC .......... *A61M 25/04* (2013.01); *A61B 17/3415* (2013.01); *A61M 25/0045* (2013.01); *A61M 25/0082* (2013.01); *A61N 1/057* (2013.01); *A61N 1/0558* (2013.01); *A61M 25/02* (2013.01); *A61M 2025/0046* (2013.01); *A61M 2025/028* (2013.01); *A61M 2025/0286* (2013.01); *A61N 2001/0582* (2013.01)

(58) Field of Classification Search
CPC ......... A61M 25/02; A61M 2025/028; A61M 2025/0286; A61M 2025/0213; A61M 2025/0293; A61M 25/04; A61M 25/0612; A61M 25/0662; A61N 1/0558; A61N 1/05; A61N 1/057
USPC ........................................ 606/108, 129, 175
See application file for complete search history.

(56) References Cited

U.S. PATENT DOCUMENTS

| | | | |
|---|---|---|---|
| 4,676,782 A | 6/1987 | Yamamoto et al. | |
| 4,699,611 A * | 10/1987 | Bowden | A61F 2/04 604/105 |
| 5,713,858 A | 2/1998 | Heruth et al. | |
| 8,262,624 B2 | 9/2012 | Sage et al. | |
| 2007/0191865 A1* | 8/2007 | Pappas | A61F 2/966 606/108 |
| 2008/0275401 A1 | 11/2008 | Sage et al. | |
| 2009/0248054 A1 | 10/2009 | Sage et al. | |
| 2011/0040257 A1 | 2/2011 | Behymer et al. | |
| 2011/0282289 A1 | 11/2011 | Lieberman et al. | |
| 2012/0232624 A1 | 9/2012 | Sage et al. | |
| 2013/0012989 A1 | 1/2013 | Sage et al. | |

FOREIGN PATENT DOCUMENTS

| | | |
|---|---|---|
| EP | 0865799 | 9/1998 |
| WO | WO2012/103123 | 8/2012 |

* cited by examiner

*Primary Examiner* — Katherine M Shi
(74) *Attorney, Agent, or Firm* — Rick L. Franzen

(57) ABSTRACT

An introducer assembly that may be employed to implant a medical device includes an introducer shaft, and an anchor sleeve and a deployment tool mounted on the shaft. According to some methods, the sleeve is deployed onto an elongate body of the medical device, after the body has been advanced through a lumen of the introducer shaft and to an implant site within a body of a patient, by pulling the introducer shaft proximally, out from the body of the patient, while holding the deployment tool in place, relative to the advanced body of the device.

13 Claims, 6 Drawing Sheets

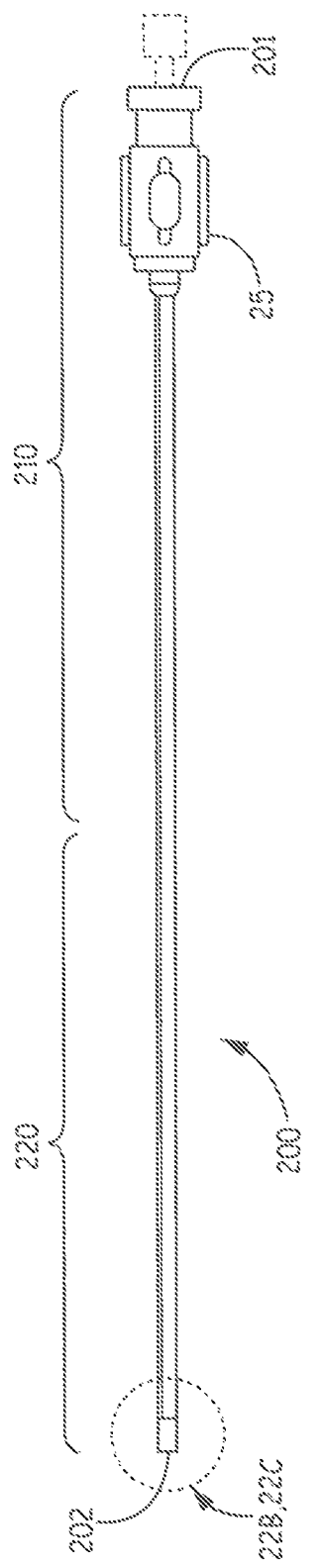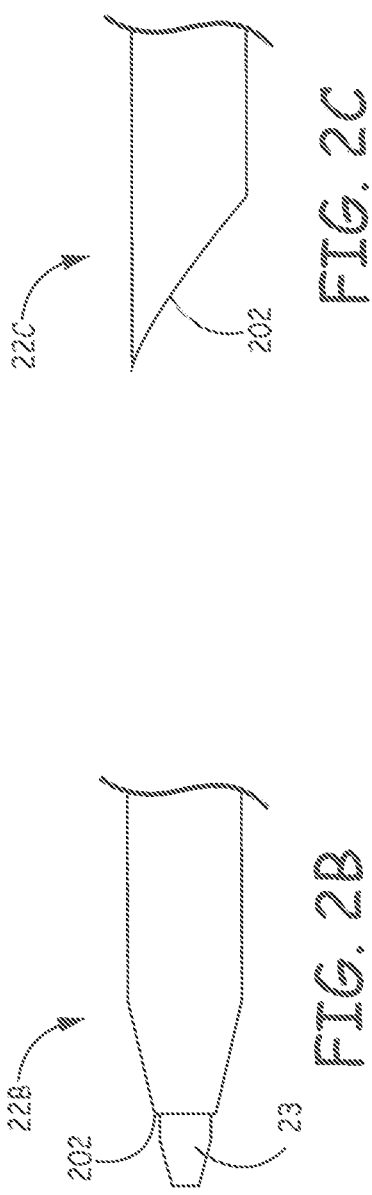

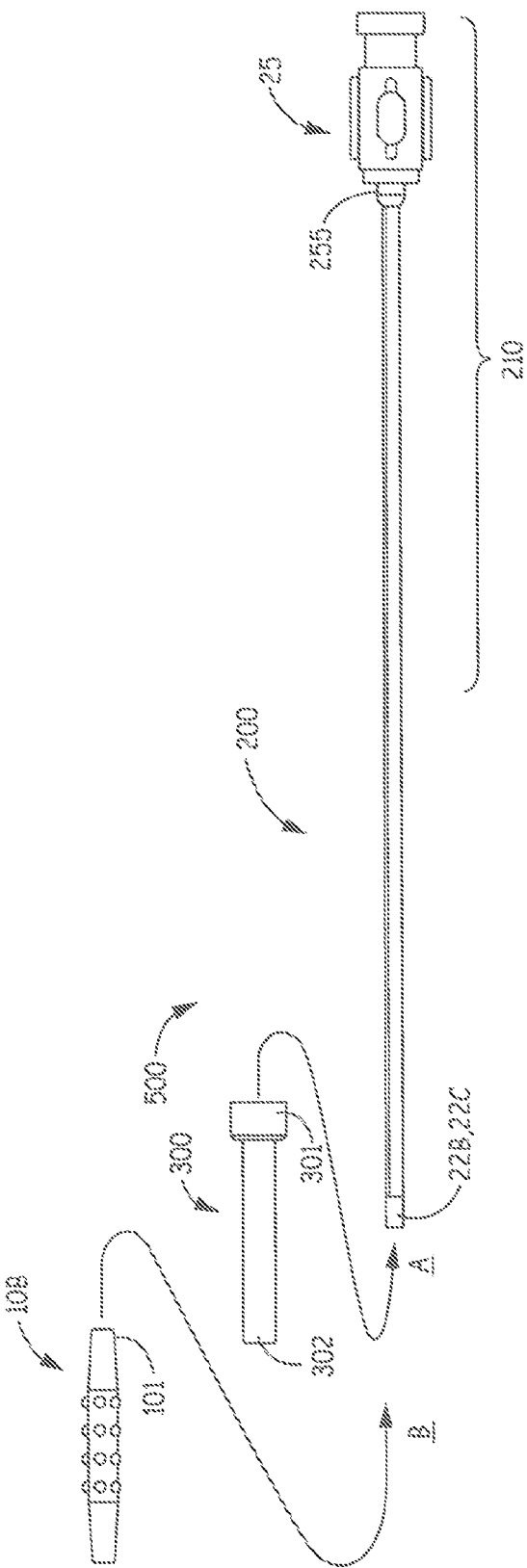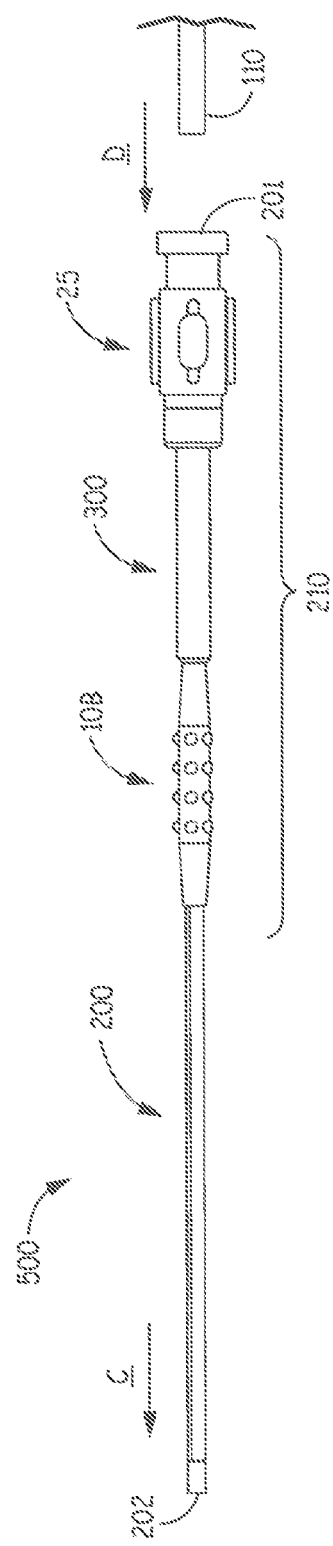
FIG. 3A
FIG. 3B

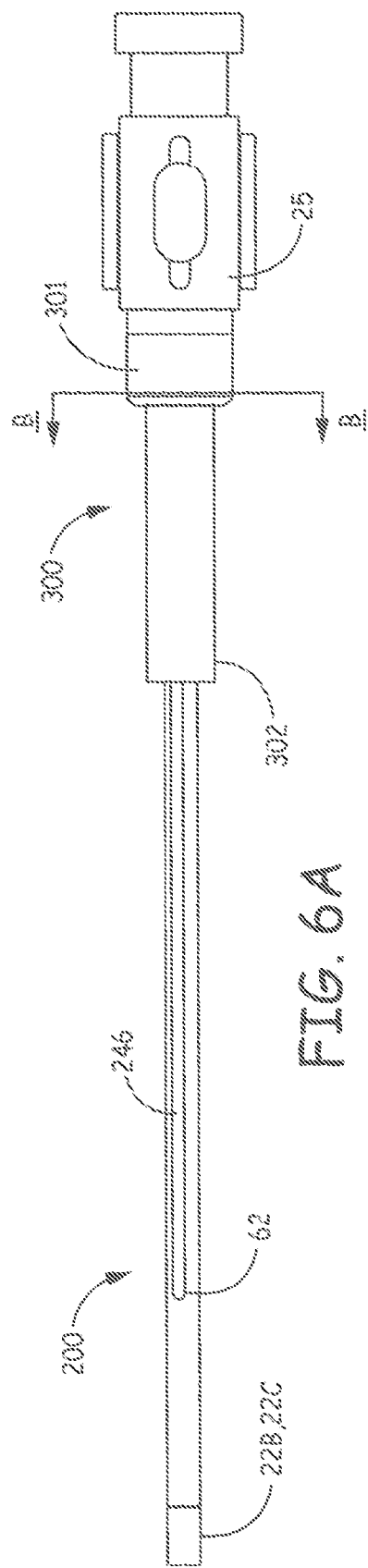
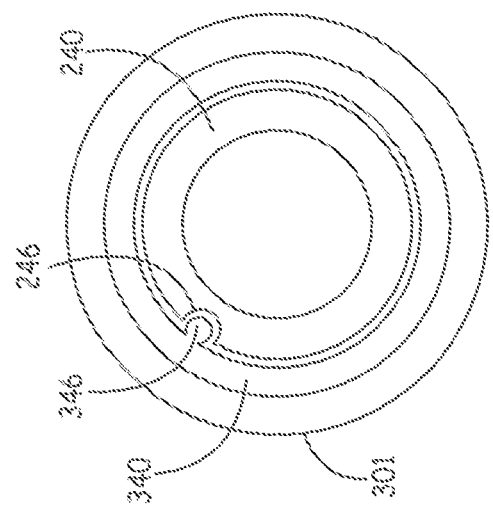
FIG. 6A
FIG. 6B

ANCHOR SLEEVE DEPLOYMENT FOR IMPLANTABLE MEDICAL DEVICES

TECHNICAL FIELD

The present disclosure pertains to implantable medical devices, and more particularly to methods and apparatus for the deployment of anchor sleeves thereon.

BACKGROUND

A variety of elongate implantable medical devices, for example, drug delivery catheters and medical electrical leads, are known in the art, for example, to couple a therapy delivery generator and/or diagnostic devices to a target site within a body of a patient, for example, in the spinal column or in the venous system, or in any of a number of internal organs. Those skilled in the art are familiar with apparatus and methods for anchoring these implanted devices. FIG. 1A is a schematic depicting an implant access site 12, for example, formed by a surgical incision, through which an elongate body 110 of an exemplary medical device has been implanted. Alternately site 12 may be a less invasive one, for example, formed via percutaneous puncture with a needle. FIG. 1A illustrates a length of device body 110 extending proximally out from site 12 and an anchor sleeve 10 surrounding body 110, for example, with a relatively tight, interference fit, to facilitate anchoring of device body 110 to subcutaneous fascia 14, for example, via sutures tied thereabout and sewn into the fascia 14, Anchor sleeve 10 may be any of a variety of types known in the art, such as types 10A, 10B and 10C shown in FIG. 1B, which are typically formed from a medical grade silicone rubber. In order to properly position such a snug fitting anchor sleeve 10 around body 110 of the implanted device, an anchor deployment tool may be employed. Examples of such a tool are described in a co-pending and commonly assigned United States Patent Publication No. 2011/0040257 (U.S. Ser. No. 12/896,147).

BRIEF DESCRIPTION OF THE DRAWINGS

The following drawings are illustrative of particular embodiments of the present disclosure and therefore do not limit the scope. The drawings are not to scale (unless so stated) and are intended for use in conjunction with the explanations in the following detailed description. Embodiments will hereinafter be described in conjunction with the appended drawings wherein like numerals/letters denote like elements, and:

FIG. 2A is a plan view of an exemplary introducer shaft, which may be included in an introducer assembly, according to some exemplary embodiments;

FIGS. 2B-C are enlarged detail views of shaft distal tips, according to alternate exemplary embodiments of the introducer shaft shown in FIG. 2A;

FIG. 3A is a plan view of parts of an introducer assembly, prior to being assembled together, according to some exemplary embodiments;

FIG. 3B is a plan view of an exemplary introducer assembly, according to some embodiments;

FIG. 6A is a plan view of an exemplary introducer assembly, according to some embodiments; and FIG. 6B is a cross-section view of a portion of the assembly of FIG. 6A, taken along line B-B, according to some exemplary embodiments.

DETAILED DESCRIPTION

Figure 1A:
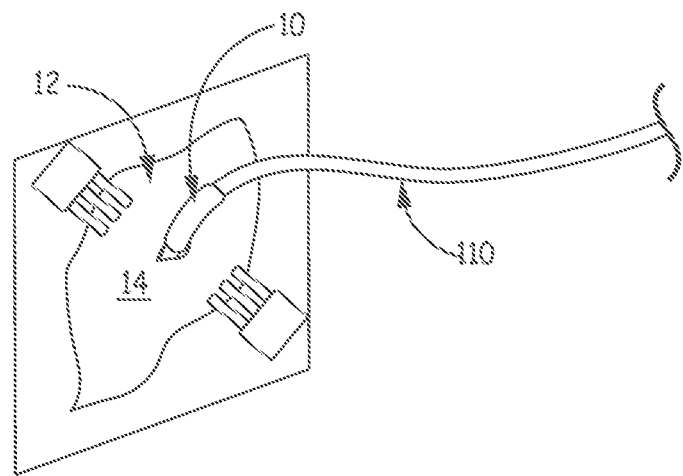
FIG. 1A is a schematic depicting an implant access site through which an exemplary elongate medical device has been implanted.
Figure 1B:
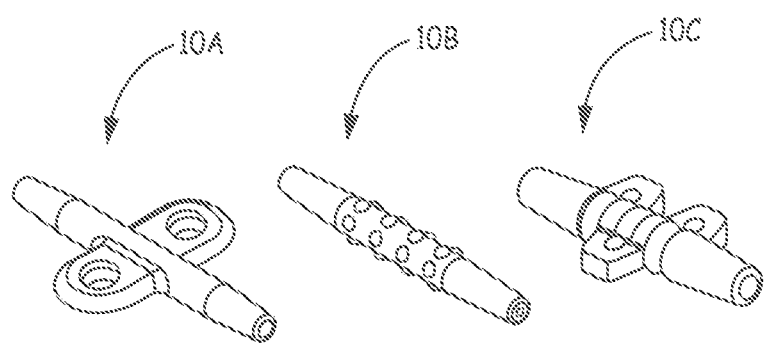
FIG. 1B is a perspective view of a variety of types of exemplary anchor sleeves.

The following detailed description is exemplary in nature and is not intended to limit the scope, applicability, or configuration of the disclosure in any way. Rather, the following description provides practical examples, and, after reading the present disclosure, those skilled, in the art will recognize that some of the examples may have suitable alternatives.

FIG. 2A is a plan view of an exemplary introducer shaft 200, which may be employed for anchor sleeve deployment, according to some embodiments and methods that are disclosed herein. FIG. 2A illustrates shaft 200 extending between a hub 25, formed at a proximal end thereof, and a tapered distal tip 22B, 22C. Those skilled in the art are familiar with several types of introducer shafts, like shaft 200, which are employed to gain percutaneous access, for example, into a spinal column or venous system of a patient's body. According to the illustrated embodiment, shaft 200 includes a lumen (not shown) extending from a proximal opening 201 formed in hub 25 to a distal opening 202 formed in distal tip 22B, 22C, so that, once a distal portion 220 of shaft 200 is inserted into the patient's body, an elongate body of a medical device, for example, body 110 (FIG. 1A), may be inserted and advanced through the lumen to an implant site. According to some embodiments of introducer assemblies, described below, a wall 240 (FIG. 4) of shaft 200 is formed by a relatively flexible polymer tube, which may have a more rigid dilator (suggested with dashed lines in FIG. 2A) slidably engaged within the lumen thereof, to facilitate initial insertion of shaft into the patient's body by lending more rigidity, or stiffness, to shaft 200; once shaft 200 is inserted, the dilator may be removed to make way for the elongate body of the medical device. Alternately, wall 240 of introducer shaft 200 may be formed by a metal tube, for example, like percutaneous needle introducers known in the art. With reference to FIG. 2B, the enlarged view of tapered distal tip 22B corresponds to the polymer tube embodiment of shaft 200, wherein a distal tip 23 of the aforementioned optional dilator is shown protruding from distal opening 202 of the lumen. With reference to FIG. 2C, the enlarged view of tapered distal tip 22C corresponds to the metal tube embodiment of shaft 200, wherein a relatively sharp point terminates tip 22C at distal opening 202 of the lumen.

FIG. 3A is a plan view of parts of an introducer assembly 500, prior to being assembled together, according to some embodiments; and FIG. 3B is a plan view of introducer assembly 500, according to some embodiments. FIGS. 3A-B illustrate assembly 500 including introducer shaft 200, a deployment tool 300, and anchor sleeve 10B. With reference to FIG. 3A, according to some methods, deployment tool 300 and anchor sleeve 10B are mounted around shaft 200 per arrows A and B, respectively. FIG. 3A shows a proximal end 301 of tool 300 oriented toward distal tip 22B, 22C of shaft 200 so that shaft 200 may be inserted into a longitudinally extending lumen (not shown) of tool 300; and, likewise, a proximal end 101 of sleeve 10B oriented toward distal tip 22B, 22C for subsequent insertion of shaft 200 into a longitudinally extending lumen (not shown) of sleeve 10B. With reference to FIG. 3B, deployment tool 300 and anchor sleeve 10B are positioned around a proximal portion 210 of shaft 200, such that tool 300 is located between sleeve 10B and hub 25 of shaft 200. It should be noted that, according to some alternate methods and embodiments, deployment tool 300 may be configured to open or expand in a radial direction for the assembly thereof about shaft 200. With reference back to FIG. 2B, when introducer shaft 200 is formed by a polymer tube and includes a dilator engaged therein, the protruding distal tip 23 of the dilator forms a more tapered leading edge, for initial insertion of shaft 200 through the lumen of sleeve 10B, that may facilitate the mounting of sleeve 10B.

With further reference to FIG. 3B, introducer assembly 500, which may be provided in a sterile package or kit, for example, similar to those in which conventional introducer shafts are packaged, may be inserted by an operator to gain implant access to a patient's body, per arrow C, according to methods known to those skilled in the art. Subsequently, the operator may insert elongate body 110 of the medical device through the lumen of shaft 200 and simultaneously through the lumen of the positioned deployment tool 300, per arrow D, and then simultaneously advance body 110 through the lumen of shaft 200, and anchor sleeve 10B, to the implant site, also per arrow D.

Figure 4:
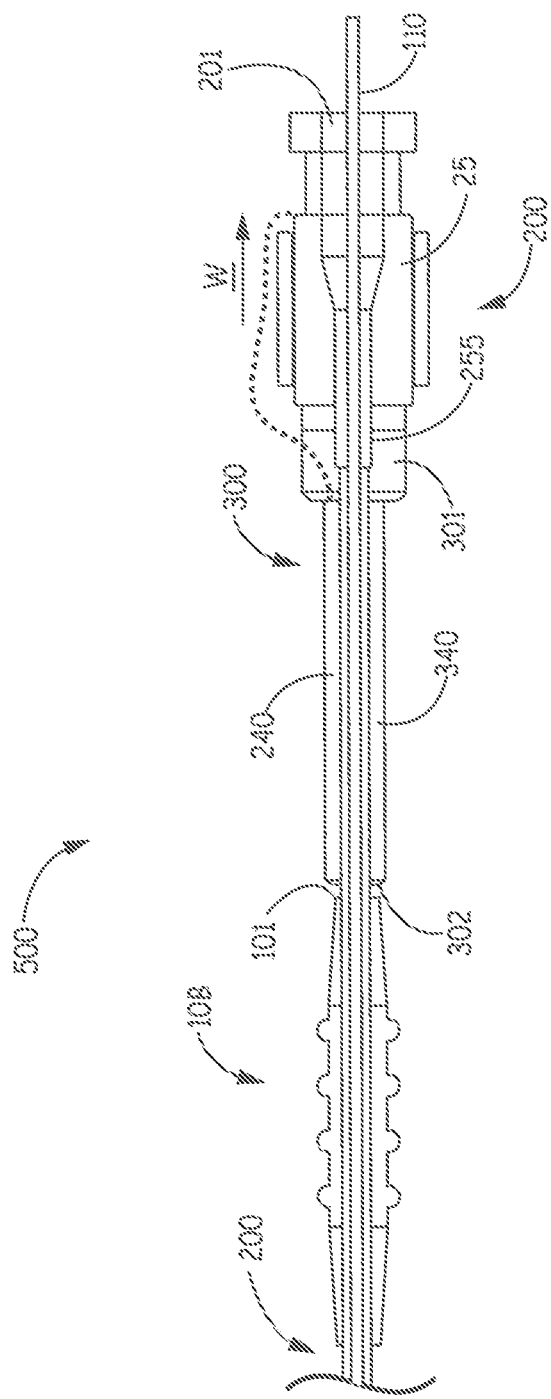
FIG. 4 is a cross-section view of a portion of the assembly of FIG. 3B, taken along a longitudinal axis thereof, according to some exemplary embodiments.

FIG. 4 is a cross-section view of a portion of assembly 500, taken along a longitudinal axis thereof, according to some embodiments. FIG. 4 illustrates proximal end 301 of deployment tool 300 mated with a shoulder 255 of hub 25, for example, via a press fit, which temporarily holds tool 300 in place relative to shaft 200. FIG. 4 further illustrates a distal end 302 of the positioned tool 300 being configured to contact proximal end 101 of the positioned sleeve 10B for the deployment thereof, as shaft 200 is moved proximally, per arrow W. Deployment tool 300 preferably includes a relatively rigid sidewall 340, which may be formed by a metal hypo-tube and/or a relatively rigid plastic, such as nylon, polyether ether ketone (PEEK), or polycarbonate. Because the lumen of anchor sleeve 10B is sized for a snug fit around device body 110, sleeve 10B, which is formed from an elastic material (e.g., medical grade silicone rubber), is stretched for mounting around introducer shaft 200; thus, according to the illustrated embodiment, an inner diameter of sidewall 340, at least at distal end 302, is sized for a relatively snug fit around shaft 200, for example, a line-iodine fit, so that distal end 302 of tool 300 may effectively contact proximal end 101 of the mounted anchor sleeve 10B to deploy anchor sleeve 10B from around shaft 200, as will be described below. Although the contact between distal end 302 of deployment tool 300 and proximal end 101 of anchor sleeve 10B is illustrated as a confronting abutment of the ends, tool 300 may be configured for alternate types of contact, for example, being tapered to wedge between proximal end 101 of sleeve 10B and shaft 240, so long as the contact is effective to hold sleeve 10B in place, relative to body 110, as shaft is moved per arrow W.

According to some exemplary embodiments, introducer shaft 200 includes a lubricious interface with deployment tool 300 and/or anchor sleeve 10B. If wall 240 of shaft 200 is formed by a polymer tube, for example, high density polyethylene (HDPE), the lubricious interface may be a coating, for example, fluorinated ethylene propylene (FEP), Polytetrafluoroethylene (PTFE), Ethylene tetrafluoroethylene (ETFE), or Polyether block amide (e.g., Pebax®), that extends over an outer surface of wall 240. If wall 240 of shaft 200 is formed by a metal needle, the lubricious interface may be a PTFE coating. Sidewall 340 of deployment tool 300, according to some embodiments, may be formed with a lubricious inner liner, for example, PTFE or HDPE, that extends along the snug fitting portion thereof.

Figure 5:
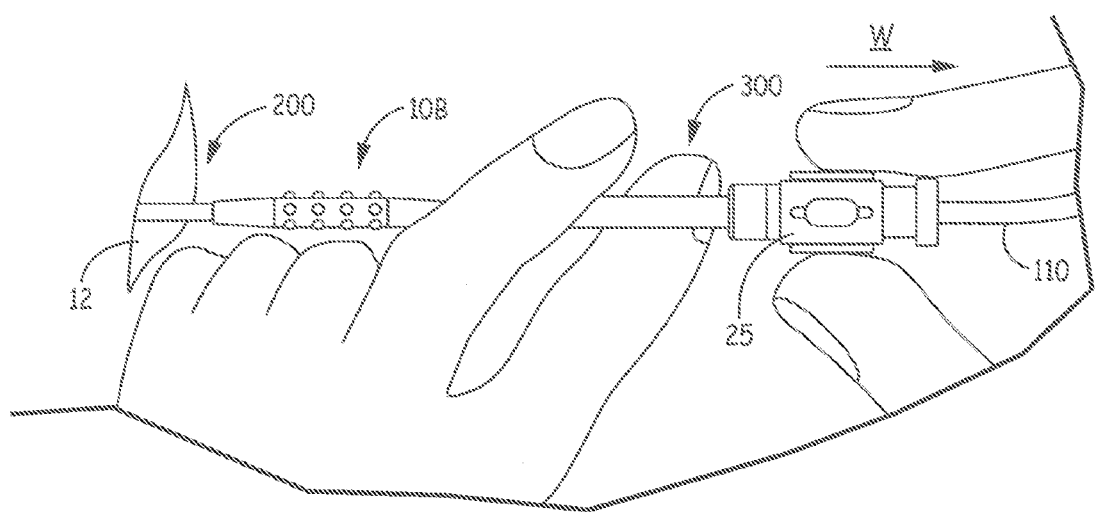
FIG. 5 is a schematic depicting an operator's hands engaged with an exemplary introducer assembly, according to some exemplary methods.

With reference to FIG. 5, which is a schematic depicting an operator's hands engaged with introducer assembly 500, the relatively rigid sidewall 340 of tool 300 is configured to support an external force, which is applied by one of the operator's hands, without transferring the force to the underlying shaft 200, while the other of the operator's hands pulls in a proximal direction, or withdraws, per arrow W, introducer shaft 200 relative to tool 300 and advanced/implanted device body 110. Thus, as shaft 200 is withdrawn, the contact of the held deployment tool 300 with proximal end 101 of sleeve 10B holds sleeve 10B in place relative to the advance/implanted device body 110 to deploy sleeve 10B onto body 110, after which tool 300 is pulled proximally, or withdrawn from body 110, so that device body is ready for anchoring, for example, as illustrated in FIG. 1A. Although the illustrated deployment tool 300 has an external surface configured to receive the fingers of the operator, according to alternate embodiments, the external surface may be configured to receive a gripping tool, for example, a forceps-like tool, which applies the external force to hold deployment tool 300 in place. It should be noted that, according to the embodiment illustrated in FIG. 4, the mating interface of proximal end 301 of tool 300 with shoulder 255 of hub 25 is simply released during the withdrawal of shaft 200 relative to device body 110.

According to some additional exemplary embodiments, a retaining feature may couple deployment tool 300 to introducer shaft 200 so that, when shaft is withdrawn from around device body 110 and sleeve 10B is left deployed thereabout, as described above, tool 300 may not be inadvertently left behind, around body 110. With reference back to FIG. 4, a dashed line depicts a tether-like feature that couples shaft 200 to tool 300, but which allows shaft to move proximally, per arrow W, relative to tool 300, far enough to allow tool 300 to deploy sleeve 10B onto body 110. The tether-like feature may be a cord, or line, with enough slack, or length, to allow adequate separation between tool 300 and hub 25 for the deployment of sleeve 10B; alternately, the tether-like feature may be elastic to stretch to the length that allows for the sleeve deployment. FIG. 6A is a plan view of an alternate embodiment, wherein shaft 200 and tool 300 include mating retaining features; and FIG. 6B is a cross-section view through section line B-B of FIG. 6A. FIG. 6A illustrates wall 240 of shaft 200 including a recessed track or groove 246, which is formed in an exterior surface thereof and is sized to mate with an inward projecting nub or tooth 346 of tool 300, which may be formed in wall 340 of tool 300 and seen in the cross-section view of FIG. 6B, According to the illustrated embodiment, tooth 346 is located at section line B-B, in proximity to proximal end 301 of tool 300, and just distal to shoulder 255 of hub 25 of shaft 200 (FIG. 4), when tool 300 is mounted on shaft 200, FIG. 6A further illustrates groove 246 terminated just proximal to distal tip 22B, 22C of shaft 200 to form a retaining stop 62 for tooth 346, so that shaft 200 and tool 300 may not be easily separated from one another after shaft 200 has been moved proximally with respect to tool 300 to deploy sleeve 10B around device body 110, as described above.

In the foregoing detailed description, specific exemplary embodiments have been described. However, it may be appreciated that various modifications and changes can be made without departing from the scope of the disclosure as set forth in the appended claims.

The invention claimed is:

1. An introducer assembly for an elongate implantable medical device, the assembly comprising:
   an elongate introducer shaft extending between a proximal end thereof and a distal end thereof, the shaft including a hub, formed at the proximal end thereof, and a lumen extending along a length thereof, the lumen having a proximal opening formed in the hub and a distal opening formed at the distal end, and the distal end having a tapered profile;
   a deployment tool including a relatively rigid sidewall and being mounted around the introducer shaft, in proximity to the hub, the deployment tool extending between a proximal end thereof and a distal end thereof, and the relatively rigid sidewall being configured to support an external force that holds the deployment tool in place while the introducer shaft is moved relative thereto;
   an anchor sleeve mounted around the introducer shaft at a location in proximity to the mounted deployment tool, such that the mounted deployment tool is located between the hub of the introducer shaft and the mounted anchor sleeve; and
   a retaining feature that couples the introducer shaft to the deployment tool;
   wherein the distal end of the mounted deployment tool is configured to contact a proximal end of the mounted anchor sleeve, when the external force holds the deployment tool in place and the introducer tool is pulled in a proximal direction, relative to the deployment tool;
   the contact of the mounted deployment tool against the proximal end of the mounted anchor sleeve, in conjunction with the external force holding the deployment tool in place, allows the introducer shaft to be pulled in the proximal direction relative to the anchor sleeve, so that the sleeve is deployed therefrom; and
   the retaining feature continues to couple the introducer shaft to the deployment tool after the shaft is pulled proximally relative to the deployment tool, and when there is adequate separation between the tool and the hub of the shaft for the anchor sleeve to be deployed from the shaft.

2. The assembly of claim 1, wherein the proximal end of the deployment tool mates with the hub of the introducer shaft, and is releasable therefrom when the external force holds the deployment tool in place, and when the introducer shaft is pulled in the proximal direction.

3. The assembly of claim 1, wherein the external force is applied by fingers of an operator, and an external surface of the deployment tool is configured to receive the fingers.

4. The assembly of claim 1, wherein the introducer shaft comprises a polymer tube, and further includes a dilator slidably engaged within the lumen thereof, the dilator having a distal tip protruding from the distal opening of the lumen of the shaft.

5. The assembly of claim 1, wherein the introducer shaft includes a lubricious interface with the deployment tool and/or the anchor sleeve.

6. The assembly of claim 1, wherein the deployment tool includes a lubricious liner interfacing with the introducer shaft.

7. The assembly of claim 1, wherein the retaining feature comprises a cord with enough length to allow the adequate separation.

8. The assembly of claim 1, wherein the retaining feature comprises an elastic member that stretches to a length that allows the adequate separation.

9. The assembly of claim 1, wherein the retaining feature comprises a recessed track, formed in an exterior surface of a wall of the introducer shaft, and an inward projecting tooth, formed in a wall of the deployment tool and mating with the track, the track being terminated just proximal to the distal end of the shaft to form a stop for the tooth.

10. The assembly of claim 1, wherein the introducer shaft comprises a metal needle.

11. An introducer assembly for an elongate implantable medical device, the assembly comprising:
   an elongate introducer shaft extending between a proximal end thereof and a distal end thereof, the shaft including a hub, formed at the proximal end thereof, and a lumen extending along a length thereof, the lumen having a proximal opening formed in the hub and a distal opening formed at the distal end, and the distal end having a tapered profile;
   a deployment tool including a relatively rigid sidewall and being mounted around the introducer shaft, in proximity to the hub, the deployment tool extending between a proximal end thereof and a distal end thereof, and the relatively rigid sidewall being configured to support an external force that holds the deployment tool in place while the introducer shaft is moved relative thereto; and
   an anchor sleeve mounted around the introducer shaft at a location in proximity to the mounted deployment tool, such that the mounted deployment tool is located between the hub of the introducer shaft and the mounted anchor sleeve;
   wherein the distal end of the mounted deployment tool is configured to contact a proximal end of the mounted anchor sleeve, when the external force holds the deployment tool in place and the introducer tool is pulled in a proximal direction, relative to the deployment tool;
   the contact of the mounted deployment tool against the proximal end of the mounted anchor sleeve, in conjunction with the external force holding the deployment tool in place, allows the introducer shaft to be pulled in the proximal direction relative to the anchor sleeve, so that the sleeve is deployed therefrom; and
   the introducer shaft comprises a metal needle.

12. The assembly of claim 11, further comprising a retaining feature that couples the introducer shaft to the deployment tool after the shaft is pulled proximally, relative to the deployment tool, and when there is adequate separation between the tool and the hub of the shaft for the anchor sleeve to be deployed from the shaft.

13. The assembly of claim 12, wherein the proximal end of the deployment tool mates with the hub of the introducer shaft, and is releasable therefrom when the external force holds the deployment tool in place, and when the introducer shaft is pulled in the proximal direction.

* * * * *